United States Patent [19]

Minagawa et al.

[11] 4,199,495
[45] Apr. 22, 1980

[54] THIOLCARBONATE ESTER STABILIZERS

[75] Inventors: Motonobu Minagawa, Kosigaya; Yutaka Nakahara, Iwatsuki; Kazumi Kitsukawa, Misato, all of Japan

[73] Assignee: Argus Chemical Corp., Brooklyn, N.Y.

[21] Appl. No.: 882,082

[22] Filed: Feb. 28, 1978

[51] Int. Cl.$^2$ ............... C07C 154/00; C07C 154/02; C08K 5/38
[52] U.S. Cl. .................... 260/45.85 S; 260/455B; 252/404
[58] Field of Search ............ 260/45.85 S, 455 B, 260/45.85 H; 560/130, 138, 140, 141, 142, 145, 147, 154; 252/404

[56] References Cited
U.S. PATENT DOCUMENTS 3,786,155  1/1974  Cousserans et al. ............ 260/455 B

*Primary Examiner*—Veronica P. Hoke
*Attorney, Agent, or Firm*—Otto S. Kauder

[57] ABSTRACT

New thiolcarbonate esters are disclosed, having a molecular weight from 400 to 5,000 perferably from 600 to 1500, and containing 3 to 20 percent by weight thiolcarbonate sulfur. The thiolcarbonate esters are represented by the formula

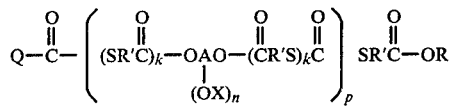

in which R is a hydrogen atom, an aliphatic hydrocarbon group having 1 to 22 carbon atoms, a cycloaliphatic hydrocarbon group having 5 to 22 carbon atoms, or an aromatic hydrocarbon group having 6 to 22 carbon atoms; R' is an alkylene group having 1 to 3 carbon atoms; A is the residue of a polyhydroxy compound having 2 to 4 carbon atoms and 2 to 4 hydroxy groups, provided that the number of hydroxy groups does not exceed the number of carbon atoms; Q is

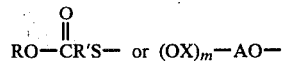

Where X individually at each occurrence is a hydrogen atom or

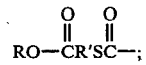

k has the same value at each occurrence and is zero or 1; m is a whole number from 1 to 3; n is a whole number from 0 to 2 and p is a number from 0 to 10.

The thiolcarbonate esters are highly effective stabilizers for a variety of synthetic resins.

Stabilizer compositions comprising a thiolcarbonate ester and a known polymer stabilizer, as well as synthetic resins stabilized with such stabilizer compositions, are also disclosed.

18 Claims, No Drawings

THIOLCARBONATE ESTER STABILIZERS

BACKGROUND OF THE INVENTION

This invention relates to a new class of S-thiolcarbonate esters and to synthetic resin stabilizer compositions comprising these esters as well as to synthetic resins stabilized with such esters and with stabilizer compositions comprising these esters along with known polymer stabilizers.

The S-thiolcarbonate esters have the characteristic group

carrying an organic group attached to sulfur and a second organic group linked to the carbonyl group through oxygen or sulfur, and can be named as carbothioic acid O,S-diesters and carbodithioic acid S,S'-diesters. The former are isomers of thiocarbonic acid O,O-diesters having the characteristic group

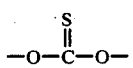

and the latter are isomers of the well known xanthate esters (carbodithioic acid O,S-diesters) having the characteristic group

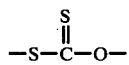

The S-thiolcarbonate esters have been remarkably little studied.

The chemical literature prior to 1940, as reviewed by M. Bogemann in Houben-Weyl, "Methoden der Organischen Chemie" (4th edition, G. Thieme Verlag Stuttgart, Germany, 1955) Volume 9, pages 816–817 and 819–820, as well as by E. E. Reid in "Organic Chemistry of Bivalent Sulfur" (Chemical Publishing Co., New York 1962) volume 4, pages 135–6 and 170–71, mentions thiolcarbonate O,S-diesters having the formula RS-CO-OR' and thiolcarbonate S,S'-diesters having the formula RS-CO-SR' in which R and R' are hydrocarbon groups such as alkyl, aryl, ethylene, or benzhydryl, as well as carboxymethyl. Both reviewers cite the ready ammonolysis and hydrolysis of these thiolcarbonates by alcoholic ammonia and hot water respectively. There is no mention, however, of higher molecular weight thiolcarbonate esters substituted with carboxyalkylenethiol groups, and the synthetic methods described are in no way applicable to the preparation of such higher molecular weight thiolcarbonate esters.

More recently, W. Dial in U.S. Pat. No. 2,537,518 of Jan. 9, 1951 disclosed esters of the general structure

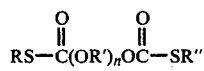

in which R and R'' are phenyl, tolyl, xylyl, and trimethylphenyl, R' is alkylene containing 2 to 4 carbon atoms, and n is a small whole number, prepared from a glycol bis(chloroformate) and a phenol or thiophenol. T. Kawata et al in Yakugaku Zasshi, volume 96 (1976), pages 832–840, described catalytic rearrangements of O,S-dialkyl dithiocarbonates to S,S'-dialkyl dithiocarbonates catalyzed by Lewis acids such as aluminum chloride, ferric chloride, stannic chloride, titanium tetrachloride, and boron trifluoride. All Kawata's thiolcarbonates had exclusively hydrocarbon substituents and no hint is given that Kawata's methods might be applicable to thiolcarbonates having other than hydrocarbon substituent groups. J. Krenzer in U.S. Pat. No. 4,040,812 of Aug. 9, 1977 disclosed compounds of the formula

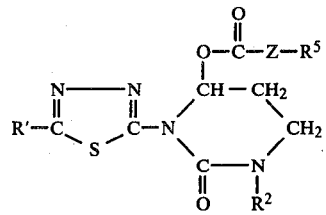

wherein $R^1$ is selected from the group consisting of lower alkyl, lower alkenyl, lower chloroalkyl, lower bromoalkyl, trifluoromethyl, lower alkoxy, lower alkylthio, lower alkylsulfonyl, lower alkylsulfinyl and cycloalkyl of from 3 to 7 carbon atoms; $R^2$ is selected from the group consisting of lower alkyl, lower alkenyl, lower chloroalkyl, lower bromoalkyl and

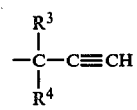

wherein $R^3$ and $R^4$ are each selected from the group consisting of hydrogen and lower alkyl; Z is selected from the group consisting of oxygen and sulfur; and $R^5$ is selected from the group consisting of lower alkyl, lower chloroalkyl, lower bromoalkyl, lower alkenyl, lower alkynyl, lower alkoxyalkyl, cycloalkyl of from 3 to 7 carbon atoms and

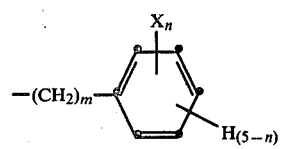

wherein X is selected from the group consisting of lower alkyl, halogen, lower haloalkyl, nitro, cyano and lower alkoxy, and m and n are each integers from 0 to 3.

T. Y. Shen et al in U.S. Pat. No. 4,057,637 of Nov. 8, 1977 disclosed compounds of structural formula

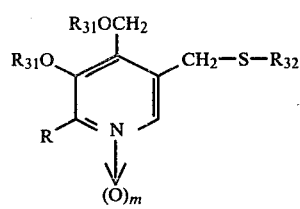

or pharmaceutically acceptable salt thereof, wherein
m is 0 or 1;
R is $C_{1-5}$alkyl;

$R_{31}$ groups are the same or different and are hydrogen

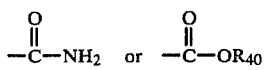

where $R_{40}$ is $C_{1-5}$alkyl or $C_{2-5}$alkenyl, $R_{32}$ is hydrogen or

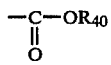

with the proviso that if both $R_{31}$ groups are hydrogen or m is 0, then $R_{32}$ is not hydrogen.

None of these disclosures includes a thiolcarbonate ester having carboxyalkylene groups linked to sulfur, and there has been no disclosure of any thiolcarbonate ester included in a synthetic resin stabilizer.

Sulfur compounds used in synthetic resin stabilizers have been mostly mercaptans, metal and organometallic mercaptans, disulfides, and thioethers such as dialkyl sulfides and thioalkylenecarboxylic acid esters.

The pioneer disclosure of thioether carboxylic acid esters for stabilizing a polymer is believed to be M. Gribbins in U.S. Pat. No. 2,519,755 of Aug. 22, 1950 of Aug. 22, 1950. Griggins stabilized ethylene polymers with 0.001% to 5% by weight of a beta-thioether of an ester of propionic acid having the formula:

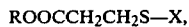

in which R is an alkyl or a cycloalkyl radical such as n- and isobutyl, amyl, heptyl, nonyl, decyl, lauryl, glycyl, cinnamyl, capryl, benzyl, allyl, cetyl, stearyl, palmityl, cyclohexyl, and similar groups, and X is:

1. a hydrocarbon group such as, e.g., the alkyl groups: methyl, ethyl, propyyl, butyl, lauryl; the aryl groups; phenyl, naphthyl, benzyl; and such groups as p-methoxy phenyl, p-hydroxyphenyl and cyclohexyl.

2. an oxygenated-hydrocarbon group such as, e.g., the alcohol groups; hydroxymethylene, hydroxyethylene, and hydroxybutylene; the ether groups; methoxymethylene, methoxyethylene and ethoxyethylene; and acid groups and the R esters thereof;

carboxymethylene, carboxyethylene, carboxypropylene and carboxybutylene; and aldehyde radicals as aldehydoethyl.

3. a sulfur-hydrocarbon group such as, e.g., mercaptoethyl, mercaptopropyl, mercaptobutyl, mercaptoisobutyl, mercaptohexyl and ethiaethyl.

4. a sulfur-and oxygenated-hydrocarbon group such as, e.g., carboxyethiaethyl $(CH_2CH_2SCH_2CH_2COOH)_2$ carboxyethiaethyldithiaethyl $(CH_2CH_2SSCH_2CH_2SCH_2CH_2COOH)$, carboxyethiaisobutyl $(CH_2CH_2CH(CH_3)SCH_2CH_2COOH)$ and carboxyethiapropyl $(CH_2CH_2CH_2SCH_2CH_2COOH)$.

5. a sulfur-and nitrogen-containing hydrocarbon group such as, e.g., 3-benzothiazyl mercaptopropionic acid, specifically described in U.S. Pat. No. 2,397,960.

Among these, Gribbins found the di-higher alkyl beta-thiodipropionates and especially the dilauryl and distearyl esters outstanding. Subsequently, thioether carboxylic acid esters and in particular thiodipropionates have been employed in conjunction with other stabilizers such as a polyhydric phenol in the stabilization of polypropylene and other polyolefins against degradation upon heating or ageing under atmospheric conditions. Disclosures by C. Tholstrup, U.S. Pat. Nos. 3,033,814 of May 8, 1962 and U.S. Pat. No. 3,160,680 of Dec. 8, 1964; L. Rayner, U.S. Pat. No. 3,181,971 of May 4, 1965; D. Bown, U.S. Pat. No. 3,242,135 of Mar. 22, 1966; S. Murdock, U.S. Pat. No. 3,245,949 of Apr. 12, 1966; H. Hagemeyer, U.S. Pat. No. 3,282,890 of Nov. 1, 1966; J. Casey, U.S. Pat. No. 3,496,128 of Feb. 17, 1970 and U.S. Pat. No. 3,586,657 of June 22, 1971; M. Minagawa, U.S. Pat. No. 3,549,572 of Dec. 22, 1970, U.S. Pat. No. 3,629,189 of Dec. 21, 1971, U.S. Pat. No. 3,673,152 of June 27, 1972, U.S. Pat. No. 3,849,370 of Nov. 19, 1974 and U.S. Pat. No. 3,869,423 of Mar. 4, 1975; W. Drake U.S. Pat. No. 3,624,026 of Nov. 30, 1971; A. DiBattista, U.S. Pat. No. 3,824,192 of July 16, 1974; B. Cook, U.S. Pat. No. 3,850,877 and H. Mueller U.S. Pat. No. 3,850,918 of Nov. 26, 1974; M. Dexter U.S. Pat. No. 3,856,748 of Dec. 24, 1974; U.S. Pat. No. 3,888,824 of June 10, 1975, and U.S. Pat. No. 3,903,160 of Sept. 2, 1975; P. Klemchuk U.S. Pat. No. 3,860,558 of Jan. 14, 1975; M. Rasberger U.S. Pat. No. 3,867,340 of Feb. 18, U.S. Pat. No. 3,901,931 of Aug. 26, 1975; H. Brunetti U.S. Pat. 3,867,337 of Feb. 18 and U.S. Pat. No. 3,873,498 of Mar. 25, 1975; S. Rosenberger U.S. Pat. No. 3,884,874 of May 20 and U.S. Pat. No. 3,887,518 of June 3, 1975; C. Ramey U.S. Pat. No. 3,907,803 of Sept. 23, 1975 are representative of a very large number of stabilizer combinations including dilauryl and distearyl thiodipropionate or other dialkyl thiodipropionates along with polyhydricphenols and sometimes organic phosphites, metallic stearates, ultraviolet absorbers, nickel compounds, and heavy metal deactivators for use in polypropylene and other polyolefins.

Thiodipropionate esters are also used in stabilizer combinations for other polymers such as elastomeric glycol-terephthalic acid polyesters disclosed by A. Bell in U.S. Pat. No. 3,157,619 of Nov. 17, 1964; high molecular weight polymers of formaldehyde disclosed by R. Green in U.S. Pat. No. 3,228,885 of Nov. 29, 1966, organotin compound stabilized polyvinyl chloride disclosed by O. Kauder in U.S. Pat. No. 3,297,629 of Jan. 10, 1967 and C. Stapfer in U.S. Pat. 3,890,276 of June 17, 1975; acrylonitrile-butadiene-styrene (ABS) polymers disclosed by W. Cummings U.S. Pat. No. 3,267,069 of Aug. 16, 1966; A. Hecker U.S. Pat. No. 3,472,813 of Oct. 14, 1969 and P. Marinacci U.S. Pat. No. 3,637,555; and polyamides disclosed by T. White in U.S. Pat. No. 3,904,705 of Sept. 9, 1975. The polyhydric phenol is believed to function as an antioxidant in such combinations, and the thiodipropionate ester is often termed a costabilizer, Secondary stabilizer, synergist, or decomposer of organic peroxides.

While dialkylthiodipropionates have many favorable attributes such as availability in high purity at reasonable cost, a low degree of toxicity, and generally good stabilizing effectiveness, certain problems attendant on their use have long been recognized, particularly the need to use high concentrations in certain highly stressed formulations to obtain the required heat stability, and a tendency to lose effectiveness in use as a result of exposure to the leaching action of moving streams of warm water and warm air as in the washing and drying cycles of automatic dishwashers and laundry machines.

Attempts to improve on these characteristics have included the use of more efficient and more permanent thiodipropionate esters as well as more effective antioxidants and stabilizer combinations. Thus A. Hecker in U.S. Pat. No. 3,244,650 of Apr. 5, 1966 disclosed a stabilizer system for polypropylene composed of three stabilizers: an organic polyhydric phenol, an organic phosphite and a polyvalent metal salt of an organic acid. To this system, U.S. Pat. No. 3,255,136 of June 7, 1966 added a fourth ingredient, a thiodipropionic acid ester having the formula:

R₁OOCCH₂CH₂—S—CH₂CH₂COOY in which R₁ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical R₂, which can be the same as or different from the R₁ radical, (c) a polymeric chain of n thiodipropionic acid ester units:

—XO(OCCH₂CH₂SCH₂CH₂COOXO)ₙOCCH₂CH₂—S—CH₂CH₂COOZ where Z is hydrogen, R₂ or M, n is the number of thiodipropionic acid ester units in the chain, and X is a bivalent hydrocarbon group of the type of R₁, that is, alkylene, alkenylene, cycloalkylene, mixed alkylene-arylene and mixed alkylene-cycloalkylene radicals: hydroxyalkylene and hydroxyalkyloxyalkylene radicals; and esters thereof with aliphatic carboxylic acids; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty atoms per sulfur atom.

U.S. Pat. No. 3,378,516, patented Apr. 16, 1968 to Tholstrup, Bell and Kibler, proposes combinations including linear thiodi alkanoate polyesters obtained from a thiodialkanoic acid and a diol having a molecular weight of from about 500 to 4000, together with a phenolic antioxidant and/or a phosphite. These combinations are said to display synergistic stabilizing effectiveness.

H. Schirmer in U.S. Pat. No. 3,598,776 of Aug. 10, 1971, disclosed that the incorporation of 10% by weight disproportionated resin in polypropylene enabled him to use 2% by weight dilaurylthiodipropionate (LTP) in the polymer without blooming while in the absence of the rosin only 1% could be used without blooming and the stability of the polymer with the rosin that the higher LTP concentration was significantly increased.

H. Schutze in U.S. Pat. No. 3,630,991 of Dec. 28, 1971 disclosed non-exuding and non-volatile sulfur containing esters of cyclic terpene alcohols for the stabilization of 2 to 8 carbon alpha-olefin polymers together with hindered phenols. Schutze's esters may be represented by the structural formulae

ROOC CH₂(CH)ₙSRₐ

ROOC CH₂(CH₂)ₙSS(CH₂)ₙCH₂COOR'

ROOCCH₂(CH₂)ₙS(CH₂)ₙCH₂COOR'

ROOC CH₂(CH₂)ₙS(CH₂)ₙS(CH₂)ₙCH₂COOR'

ROOC CH₂(CH₂)ₙS(CH₂)ₙS(CH₂)ₘCH₃ where

Rₐ is —CH₂(CH₂)ₙCOOR' or alkyl
n=1 to 5
m=1 to 16
R is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, V-terpineyl, methyl, and dihydroterpineyl, and R' is a radical selected from the group consisting of abietyl, hydroabietyl, tetrahydroabietyl, dihydroabietyl, dehydroabietyl, dihydropimaryl, tetrahydropimaryl, borneyl, alpha-terpineyl, B-terpineyl, methyl, and dihydroterpineyl.

A. Onishi, in U.S. Pat. No. 3,629,194 of Dec. 21, 1971 disclosed a polyolefin resin stabilized against thermal aging with esters of alkyl thiopropionic or alkyl thiobutyric acid with a polyol having up to five hydroxyl groups, in combination (optionally) with a phenolic antioxidant. The alkyl thiopropionic or alkyl thiobutyric acid esters are defined as having one of the formulae:

R-SCₙH₂ₙCOOR'OOCCₙH₂ₙSR                     (1)

RSCₙH₂ₙCOOCₘH₂ₘSCₘH₂ₘOOCCₙH₂ₙSR          (2)

R''C(CH₂OX)₃                                 (3)

$$\begin{array}{c} CH_2OX \\ | \\ HC-OX \\ | \\ CH_2OX \end{array}$$ (4)

and

C—CH₂OX)₄                                    (5)

wherein
R is an alkyl of 8 to 30 carbon atoms,
m and n are each integers of 2 or 3,
R' is an alkylene containing 2 to 12 carbon atoms,
R'' is an alkyl containing 1 to 20 carbon atoms,
X is hydrogen or —OC—CₙH₂ₙSR, at least one of which is —OCCₙH₂ₙSR,
the R₁,R' and R'' moieties in one compound being the same or different.

The phenolic antioxidants are defined by Onishi as mono-or polyhydric phenolic compounds in which at least one of the ortho positions to a hydroxyl group is substituted by an alkyl, aralkyl, or cycloalkyl group.

The substituents preferably contain carbon atoms of a number of the order of 3 to 10, and the alkyl group, inclusive of that in an aralkyl and cycloalkyl groups can be unsaturated. The phenolic compounds may be further substituted, and the phenolic compounds may be polyphenolic compounds such as bisphenolic, trisphenolic, or tetrakisphenolic compounds in which phenolic nuclei are connected by a connecting group such as an alkylene, a thioether, or a triazinoxyl group.

M. Dexter in U.S. Pat. No. 3,758,549 of Sept. 11, 1973 disclosed alkyl esters derived from alkyl thioalkanoic acids and alkane polyols, such as pentaerythritol tetrakis, 3-n-dodecylthiopropionate, and ethylene-bis-3-n-dodecylthiopropionate. These are used in combination with phenolic antioxidants to effectively stabilize polyolefins from the deleterious effects of heat and oxygen. The alkyl esters are defined by the formula:

$$\left( R-S-CH_2CH_2\overset{\overset{O}{\|}}{C}O \right)_n Z$$

wherein

R is an alkyl group of from one to eighteen carbon atoms, n has a value of from 2 to 4; and Z is an aliphatic hydrocarbon of the formula:

$$C_yH_{2y+2-n}$$

In which y has a value of from 2 to 18 when n is 2 and a value of from 3 to 6 when n is greater than 2, the value of y is all cases being equal to or greater than that of n.

M. Minagawa in Japanese Kokai 75/106881 of Aug. 27, 1975 disclosed stabilized resin compositions containing 3-alkylthiopropionate esters of alcohols containing a nitrogen-heterocyclic ring, for example tris(2-hydroxyethyl isocyanurate) and optionally a phenolic antioxidant.

E. Schurdak in U.S. Pat. No. 3,966,675 of June 29, 1976 has disclosed mixtures of pentaerythritol tetrakis(3-n-dodecylthiopropionate) with bis(4-t-butyl-3-hydroxy-2,6-dimethylbenzyl) dithiolterephthalate or 1,3,5-tris(4-t-butyl-3-hydroxy-2,6-dimethylbenzyl)-s-triazine-2,4,6-trione that are stated to be extremely effective in inhibiting the thermal degradation of polypropylene.

There have also been disclosures of improved stabilization of olefin polymers, vinyl chloride polymers, and other synthetic resins with thiodipropionate esters used together with special phenolic condensation products. Thus D. Bown et al. in U.S. Pat. No. 3,510,507 of May 5, 1970 and U.S. Pat. No. 3,691,132 of Sept. 12, 1972 disclosed polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula, $$\left[ H \overset{}{\underset{}{-}} O \underset{R'}{\overset{R'''}{\underset{R''''}{\bigcirc}}} X \underset{R'}{\overset{R'''}{\underset{R''''}{\bigcirc}}} O-Y \right]_n Z$$

where X is selected from the group consisting of $$-S-, \quad -\underset{R}{\overset{R}{\underset{|}{C}}}-, \quad -\overset{O}{\underset{\|}{C}}-,$$

—C—C, and C—A—C— where A is a $C_1$ to $C_{16}$ alkylene or an arylene; R', R'', R''', and R'''' are selected from the group consisting of hydrogen, $C_1$ to $C_{18}$ alkyls, and an aryl group; Y is selected from the group of $$-P-, \quad -\overset{O}{\underset{\|}{P}}-, \quad -P-, \quad -\overset{O}{\underset{\|}{P}}-, \quad \text{and} \quad -B-$$
$$\underset{OR}{|} \quad \underset{OR}{|} \quad \underset{R}{|} \quad \underset{R}{|} \quad \underset{OR}{|}$$

where R is hydrogen, a $C_1$ to $C_{18}$ alkyl, or aryl;

$$-\overset{O}{\underset{\|}{C}}-, \quad -\overset{O}{\underset{\|}{C}}-(CH_2)_m-\overset{O}{\underset{\|}{C}}-$$

where m is 0 to 10, preferably 4 to 8, $$-\overset{O}{\underset{\|}{C}}-A'-\overset{O}{\underset{\|}{C}}-$$

where A' is $(CH_2)_n$—S—$(CH_2)_n$ or —$(CH_2)_n$—S—$(CH_2)_m$—S—$(CH_2)_n$ where n is 0 to 10, preferably 2 and m is 0 to 10, preferably 5;

$$-\underset{R}{\overset{R}{\underset{|}{Si}}}- \quad \text{and} \quad -\underset{R}{\overset{R}{\underset{|}{Si}}}-O-\underset{R}{\overset{R}{\underset{|}{Si}}}-$$

where R is an alkyl, preferably methyl, and Z is $$-O \underset{R'}{\overset{R''''}{\underset{R'''}{\bigcirc}}} X \underset{R'}{\overset{R''''}{\underset{R'''}{\bigcirc}}} -OH$$

where R', R'', R''', R'''', and X correspond respectively to the R',R'',R''',R'''', and X previously selected when n has a value from 1 to 15, or Z may be derived from the compound used to introduce Y into the product when n has a value from 2 to 15, for example —R or —OR where R is hydrogen, an alkyl, or aryl. When Y in the formula of Bown's stabilizer is $$-P-,$$
$$\underset{OR}{|}$$

the stabilizer is a type of hydroxyaryl phosphite. Similarly, when Y in the formula is $$-\overset{O}{\underset{\|}{C}}-,$$

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto) paraxylylene, and 10,24-dithiotetracontane.

J. Floyd et al U.S. Pat. No. 4,032,510 of June 28, 1977, disclosed low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris(nonylphenyl) phosphite, and distearyl pentaerythritoldiphosphite.

SUMMARY OF THE INVENTION

In accordance with this invention, carboxyalkylene and hydrocarbyloxycarbonylalkylene thiolcarbonate esters having a molecular weight from 400 to 5000 and preferably from 600-2000, a thiolcarbonate sulfur content from 3 to 20 percent by weight, and at least one S-carboxyalkylene, or one S-hydrocarbyloxy-carbonylalkylenethiolcarbonate ester group having 1 to 22 carbon atoms in the hydrocarbyloxy group, and 1 to 3 carbon atoms in the alkylene group are prepared. The thiolcarbonate esters of the invention can optionally contain polyhydric phenol or polyhydric alcohol groups in the molecule and are represented by the formula:

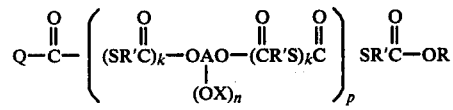

in which R is a hydrogen atom, an aliphatic hydrocarbon group having 1 to 22 carbon atoms, a cycloaliphatic hydrocarbon group having 5 to 22 carbon atoms, or an aromatic hydrocarbon group having 6 to 22 carbon atoms; R' is an alkylene group having 1 to 3 carbon atoms; A is the residue of a polyhydroxy compound having 2 to 40 carbon atoms and 2 to 4 hydroxy groups, provided that the number of hydroxy groups does not exceed the number of carbon atoms; Q is

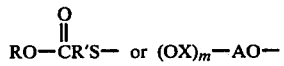

where X individually at each occurrence is a hydrogen atom or

k has the same value at each occurrence and is zero or 1; m is a whole number from 1 to 3; n is a whole number from 0 to 2; and p is a number from 0 to 10.

Synthetic resin stabilizer compositions comprising a thiolcarbonate ester of this invention contain at least one known polymer stabilizer along with one or more thiolcarbonate esters of this invention. The proportions of thiolcarbonate ester to known polymer stabilizer in such stabilizer compositions can range form about 20 to 1 to about 1 to 20 by weight. Stabilized synthetic resin compositions comprising thiolcarbonate ester of this invention contain 0.01 to 5% thiolcarbonate by weight of the resin.

DESCRIPTION OF THE PREFERRED EMBODIMENTS

The thiolcarbonate esters of this invention are characterized by the presence in of the molecule of at least one thiolcarbonate group

which links together two organic groups. The organic-group linked to sulfur in at least one occurrence is a carboxy alkylene group having 1 to 3 carbon atoms in the R' alkylene group and optionally an esterifying R group of 1 to 22 carbon atoms. The second organic group is linked to the carbonyl carbon of the thiolcarbonate group through oxygen or sulfur and can be a carboxy alkylene group similar to the sulfur-linked group defined above; a hydroxycarbyloxycarbonylalkylene group in which the hydrocarbyl segment is a two-valent A group linked by way of a carboxyalkylenethio group to a second thiolcarbonate ester group; the residue of a polyhydroxy compound having 2,3, or 4 alcoholic or phenolic hydroxyl groups and 2 to 40 carbon atoms, provided that no carbon atom can bear more than one hydroxyl group and there are, accordingly, no more hydroxyl groups than carbon atoms; an S-alkylenecarboxylate ester of such a polyhydroxy compound; and a carbonate ester of such a polyhydroxy compound.

The alkylene group R' can be methylene, ethylene, ethylidene, propylene, 1-methylethylene, and 2-methylethylene.

Hydrocarbon R groups can be alkyl, alkenyl, cycloalkyl, cycloalkenyl, aryl, aralkyl, and alkaryl groups having up to 22 carbon atoms. Useful alkyl groups subject to the above molecular weight limitation, include methyl, ethyl, 1- and 2-propyl, 1- and 2-butyl, 2-methyl-1-propyl, 2-ethyl-1-butyl, 2-ethyl-1-hexyl, 1-octyl, isooctyl, nonyl, n-decyl, isodecyl, 1-dodecyl, 1-tridecyl, isotridecyl, 1-tetradecyl, 1-hexadecyl, 2-butyl-1-decyl, eicosanyl and docosanyl. Alkenyl groups useful for R include allyl, crotyl, methallyl, 10-undecen-1-yl, and linoleyl. Useful cycloalkyl groups include cyclopentyl, cyclohexyl, 3,3,5-trimethylcyclohexyl, cyclooctyl, cyclododecyl, and isobornyl. Useful aryl, aralkyl, and alkaryl groups include phenyl, benzyl, tolyl, p-cumylphenyl, p-dodecylbenzyl, di-t-butylphenyl and di(alphamethylbenzyl)phenyl. R can also be hydrogen.

The polyhydroxy compound whose residue A can be part of a thiolcarbonate ester according to this invention can be open chain or cyclic, with alcoholic and phenolic hydroxyl groups. Useful open chain polyhydroxy compounds include alkanediols such as ethane-1,2-diol, propane-1,2-diol, 2,2-dimethylpropane-1,3-diol, butane-1,3- and -1,4-diols, and 2-ethylhexane-1,3-diol; open chain diols with oxygen or sulfur atoms as part of the chain, for example 2,2'-oxydiethanol, 2,2'-thio-diethanol, dipropylene glycol, triethylene glycol, tetraethylene and higher polyethylene glycols; 3-functional and 4-functional alcohols such as glycerol, trimethylolethane, diglycerol, and pentaerythritol. Useful cyclic polyhydric alcohols include cycloaliphatic diols such as 1,1,3,3-tetramethylcyclobutane-2,4-diol cyclohexane-1,4-dimethanol and cyclooctane-1,5-diol; and dihydroxy compounds having alcoholic hydroxyl groups linked through an aromatic ring, such as p-xylylenediol, 4,4′-isopropylidenebis(phenoxyethan-2-ol) and bis(2-hydroxyethyl) terephthalate.

Phenolic polyhydroxy compounds that can be used include 4,4′-isopropylidenediphenol, 4,4′-thiobisphenol, 4,4′-sulfonylbisphenol, and preferably ortho hydrocarbon substituted derivatives of these and other polyhydric phenols.

When A is a residue of a polyhydric phenol, A can be represented by the formula

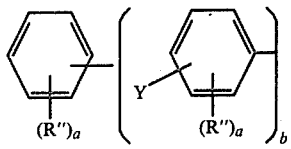

in which independently at each occurrence R″ is an alkyl, cycloalkyl, or aralkyl radical having not over 10 carbon atoms, Y is a single bond, oxygen, sulfur,

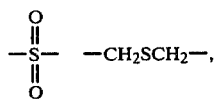

a bivalent hydrocarbon radical,

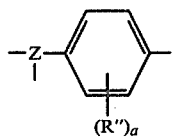

where Z is a hydrocarbon radical, a is a whole number from 0 to 3, and b is zero or one.

Illustrative of a preferred class of carboxyalkylenethiolcarbonate esters of this invention is the class of thiolcarbonate esters derived from ortho-substituted 1,3- and 1,4-dihydric phenols having one benzenoid ring, such that in the formula of A, a is at least 1 and b is zero, for example 2,5-di-t-butylhydroquinone, 2,3,6-trimethylhydroquinone, 2-methylresorcinol, and 2,6-di-t-butylresorcinol. Another preferred class of thiolcarbonate esters of this invention is the class of thiolcarbonates derived from ortho-substituted bisphenols having two ortho-substituted phenolic groups linked directly or through a two-valent hydrocarbon group, such that in the formula of A, a is at least one, R″ is a substituent located ortho to the phenolic group, b is one, and Y is a bivalent hydrocarbon radical or a single bond, for example 2,2′-methylene bis(4-methyl-6-t-butyl-phenol), 2,2′-methylene bis(4-ethyl-6-t-butylphenol), 2,2′-ethylene bis(4-ethyl-6-t-butyl-phenol), 2,2′-methylene bis(4-methyl-6-(1-methylcyclohexyl)phenol), 2,2′-n-butylidene bis(4,6-dimethylphenol), bis-1,1-(2′-hydroxy-3′5′-dimethylphenyl)-3,5,5-trimethylhexane, 2,2′-cyclohexylidene bis (4-ethyl-6-t-butylphenol), 4,4′-bis(2,6-di-t-butylphenol), 4,4′-methylene bis(2,6-di-t-butylphenol), 4,4′-isopropylidene bis(2-phenylethylphenol), 4,4′-n-butylidene bis(3-methyl-6-t-butylphenol), 4,4′-cyclohexylidene bis(2-t-butylphenol), 4,4′-cyclohexylidene bis(2-cyclohexylphenol), and 4,4′-benzylidene bis(2-t-butyl-5-methylphenol).

A further preferred class of thiolcarbonate esters of this invention is the class of thiolcarbonates derived from ortho-substituted bisphenols having two ortho-substituted phenolic groups linked through oxygen or sulfur, such that in the formula of A, a is at least one, R″ is a substituent located ortho to the phenolic group, b is one, and Y contains oxygen or sulfur, for example 4,4′-oxobis(3-methyl-6-isopropylphenol), 4,4′-thiobis(2-methyl-6-t-butyl phenol), 4,4′-thiobis(3-methyl-6-t-butylphenol), 4,4′-sulfobis(3-methyl-6-t-butylphenol), bis (2-methyl-4-hydroxy-5-t-butylbenzyl) sulfide, bis(3,5-di-t-butyl-4-hydroxy benzyl) sulfide, 2,2′-thiobis (4-t-butyl-6-methylphenol), 2,2′-thiobis(4-methyl-6-t-butyl-phenol), and 2,2′-thiobis(4,6-di-t-butylphenol). A particularly preferred class of thiolcarbonate esters of this invention is the class of thiolcarbonates derived from ortho-substituted trisphenols having three ortho-substituted phenolic groups, such that in the formula of A, a is at least one, R″ is a substituent located ortho to each phenolic group, b is one, and Y is of the form

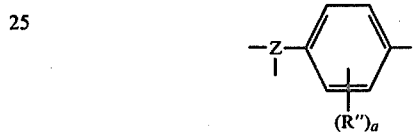

where Z is a hydrocarbon radical having at least three carbon atoms linked to each of three phenolic substituted benzenoid rings, for example 1,1,3-tris(2′methyl-4′-hydroxy-5′-t-butylphenyl)butane, 1,3,5-tris(3′,5′-di-t-butyl-4′-hydroxybenzyl)-2,4,6-trimethylbenzene, 2,2-bis(3′-t-butyl-4′-hydroxyphenyl)-4-(3″,5″-di-t-butyl-4″-hydroxyphenyl)butane, and 2,2-bis(2′-methyl-5-t-butyl-4′-hydroxyphenyl)-4-(3″,5″-di-t-butyl-4″-hydroxyphenyl) butane.

In the formula of the thiolcarbonate ester of this invention, Q is one of

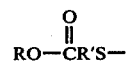

and (OX)$_m$—AO— in which R, R′, and A are as already defined and exemplified, each X independently is either hydrogen or

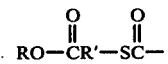

and m the number of OX groups is 1,2, or 3.

When p is zero, the formula of the thiolcarbonate ester of the invention is

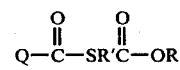

in which Q, R′, and R are previously defined, within the molecular weight & thiolcarbonate sulfur content ranges disclosed.

In the class of thiolcarbonate esters where p is zero and Q is there are two

ROCR'S—,

ROCR'S— groups in the ester and at least one of the R groups is a hydrocarbon group having at least 12 carbon atoms.

Suitable instances of this class of thiolcarbonate esters are S,S'-bis(n-hexadecyloxycarbonylmethylenethiol)carbonate, S, S'-bis(docosanyloxycarbonylethylenethiol)carbonate, and S-octadecyloxycarbonylethylenethiol-S'-carboxyethylenethiolcarbonate. In the class of tholcarbonate esters where p is zero and Q is (XO)$_m$AO—, there is one polyhydroxy compound residue A and there can be, depending on the assignment of X and m, from 1 to 4

ROCR'S— groups, in each of which independently R can be hydrogen or hydrocarbon as previously defined. Suitable instances of this class of thiolcarbonate esters are 1,4-butanebis(2-ethylhexyloxycarbonylmethylenethiolcarbonate), 4,4'-isopropylidenedicyclohexanebis(isotridecyloxycarbonylethylenethiolcarbonate), and 4-(2'-methyl-4'-hydroxy-5'-t-butyl-alphapropylbenzyl)-2-t-butyl-5-methylphenyl S-tetradecyloxycarbonylethylenethiolcarbonate.

When p is a positive number and k is one, the formula of the thiolcarbonate ester of the invention is

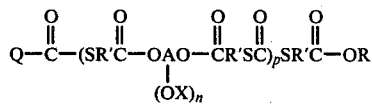

where n, Q, R, and R' are as defined above and p is a whole number from 1 to 10, within the disclosed range of molecular weight and thiolcarbonate sulfur content. Depending on the assignments of Q, X, n and p the number of

ROCR'S— thiolcarbonate ester groups in this type of ester can range from 3 up to an upper limit of 15 or even higher set by the molecular weight limit of 5000.

Suitable instances of this class of thiolcarbonate esters are the series of oligoesters of 2,2-dimethylpropanediol bis(3-thiopropionate) thiolcarbonate with 1 to 10 diol diester units terminated with n-hexadecyl 3-thiopropionate; cyclohexanel, 4-dimethanol bis(4-thiobutyrate) thiolcarbonate oligoester units terminated with 2-ethylhexyl 4-thiobutyrate, and 4,4'-isopropylidenebis(phenoxyethan-2-ol) 3-thiopropionate thiolcarbonate oligoester units terminated with p-t-butylphenyl 3-thiopropionate.

When p is a positive number and k is zero, the formula of the thiolcarbonate ester of the invention is

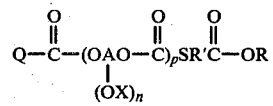

where n, Q, R, A, X, and R' are as defined above and p is a whole number from 1 to 10, within the disclosed range of molecular weight and thiolcarbonate sulfur content. Depending on the assignments of Q, X, n, and p, the number of

ROCR'S— thiolcarbonate ester groups in this type of ester can range from 1 up to an upper limit of 15 or even higher set by the molecular weight limit of 5000.

Suitable instances of this class of thiolcarbonate esters are carboxyalkylenethiolcarbonates of hydroxyl-terminated polyhydroxycompound carbonate oligoesters, such as bis(phenoxycarbonylethylenethiolcarbonate) of bis(4,4'-thiobis(2-t-butyl-5-methylphenol))carbonate and bis(1-nonyloxycarbonylethylenethiolcarbonate) of bis(3,5-di-t-butyl-4-hydroxybenzylsulfide) carbonate.

A particularly preferred group of thiolcarbonate esters of this invention is listed by name and formula in TABLE 1.

TABLE 1

THIOLCARBONATE ESTERS

No. 1

$$C_{12}H_{25}OOCC_2H_4SCSC_2H_4COOC_{12}H_{25}$$

S,S'-bis(2-dodecyloxycarbonylethylene)dithiolcarbonate
11.2% thiolcarbonate sulfur.

No. 2

$$C_{18}H_{37}OOCC_2H_4SCSC_2H_4COO(CH_2)_6OOCC_2H_4SCSC_2H_4COOC_{18}H_{37}$$

Hexamethylenebis(2-octadecyloxycarbonylethylenethiolcarbonylthiopropionate) 12.0% thiolcarbonate sulfur.

No. 3

$$C_{18}H_{37}OOCC_2H_4SCS\left(C_2H_4COO(CH_2)_6OOCC_2H_4SCS\right)_3 C_2H_4COOC_{18}H_{37}$$

Trimeric thiolcarbonate of hexamethylenebis(3-thiopropionate)
S-terminated with octadecyl 3-thiopropionate. 15.0% thiolcarbonate sulfur.

No. 4

$$C_{18}H_{37}OOCC_2H_4SCSC_2H_4COO(CH_2)_{10}OOCC_2H_4SCSC_2H_4COOC_{18}H_{37}$$

TABLE 1-continued

THIOLCARBONATE ESTERS

Decamethylenebis(2-octadecyloxycarbonylethylenethiocarbonyl-
thiopropionate) 11.5% thiolcarbonate sulfur.

No. 5
$$C_8H_{17}OOCC_2H_4\overset{O}{\underset{\parallel}{C}}SC_2H_4COOC_2H_4OC_2H_4OOCC_2H_4\overset{O}{\underset{\parallel}{C}}SC_2H_4COOC_8H_{17}$$

Oxydiethylenebis(2-octyloxycarbonylethylenethiolcarbonyl-
thiopropionate)

No. 6
$$C_{12}H_{25}OOCCH_2\overset{O}{\underset{\parallel}{C}}SCH_2COOC_2H_4SC_2H_4OOCCH_2\overset{O}{\underset{\parallel}{C}}SCH_2COOC_{12}H_{25}$$

Thiodiethylenebis(dodecyloxycarbonylmethylenethiolcarbonyl-
thioacetate)

No. 7
$$C_4H_9OOCC_2H_4\overset{O}{\underset{\parallel}{C}}SC_2H_4COO-\underset{}{\bigcirc}-\underset{\underset{CH_3}{|}}{\overset{CH_3}{\overset{|}{C}}}-\underset{}{\bigcirc}-OOCC_2H_4\overset{O}{\underset{\parallel}{C}}SC_2H_4COOC_4H_9$$

4,4′-Isopropylidenebis(phenyl 3(butoxycarbonylethylenethiol-
carbonyl)thiopropionate). 16.9% thiolcarbonate sulfur.

No. 8
$$C_{18}H_{37}OOCC_2H_4\overset{O}{\underset{\parallel}{C}}SC_2H_4COO-\underset{\times}{\overset{CH_3}{\bigcirc}}-\underset{\underset{C_3H_7}{|}}{CH}-\underset{\times}{\overset{CH_3}{\bigcirc}}-OOCC_2H_4\overset{O}{\underset{\parallel}{C}}SC_2H_4COOC_{18}H_{37}$$

4,4′-Butylidenebis(2-t-butyl-5-methylphenyl 2(octadecyloxy-
carbonylethylenethiolcarbonyl)thiopropionate. 9.7% thiolcarbonate
sulfur.

No. 9
$$\bigcirc-OOCC_3H_6\overset{O}{\underset{\parallel}{C}}SC_3H_6COO-\underset{\times}{\overset{CH_3}{\bigcirc}}-S-\underset{\times}{\overset{CH_3}{\bigcirc}}-OOCC_3H_6\overset{O}{\underset{\parallel}{C}}SC_3H_6COO-\bigcirc$$

4,4′-thiobis(2-butyl-5-methylphenyl 3(phenoxycarbonylpropylene-
thiolcarbonyl thiobutyrate). 12.4% thiolcarbonate sulfur.

No. 10
$$C_{18}H_{37}OOCC_2H_4\overset{O}{\underset{\parallel}{S}C}OCH_2-\underset{\underset{CH_3}{|}}{\overset{CH_3}{\overset{|}{C}}}-CH_2O\overset{O}{\underset{\parallel}{C}}SC_2H_4COOC_{18}H_{37}$$

2,2-dimethyl-1,3-propanebis(2-octadecyloxycarbonylethylene-
thiolcarbonate). 7.1% thiolcarbonate sulfur.

No. 11
$$C_{18}H_{37}OOCC_2H_4\overset{O}{\underset{\parallel}{S}C}\underset{}{\left[-O\;CH_2-\underset{\underset{CH_3}{|}}{\overset{CH_3}{\overset{|}{C}}}-CH_2O\overset{O}{\underset{\parallel}{C}}-\right]_2}SC_2H_4COOC_{18}H_{37}$$

Bis(2-octadecyloxycarbonylethylenethiolcarbonate) of di-2,2-
dimethyl-3-hydroxypropyl carbonate. 6.4% thiolcarbonate sulfur.

No. 12
$$C_{12}H_{25}OOCC_2H_4\overset{O}{\underset{\parallel}{S}C}O-\bigcirc-\underset{\underset{O}{\parallel}}{\overset{O}{\overset{\parallel}{S}}}-\bigcirc-O\overset{O}{\underset{\parallel}{C}}SC_2H_4COOC_{12}H_{25}$$

4,4′-sulfonylbis(phenyl 2-dodecyloxycarbonylethylenethiolcarbonate)
7.5% thiolcarbonate sulfur.

No. 13
$$C_{18}H_{37}OOCC_2H_4\overset{O}{\underset{\parallel}{S}C}O-\underset{\times}{\overset{CH_3}{\bigcirc}}-\underset{\underset{C_3H_7}{|}}{CH}-\underset{\times}{\overset{CH_3}{\bigcirc}}-O\overset{O}{\underset{\parallel}{C}}SC_2H_4COOC_{18}H_{37}$$

4,4′-butylidenebis(2-t-butyl-5-methylphenyl 2-octadecyloxycarbonyl-
ethylenethiolcarbonate). 5.6% thiolcarbonate sulfur.

No. 14
$$C_{18}H_{37}OOCC_2H_4\overset{O}{\underset{\parallel}{S}C}\underset{}{\left[-O-\underset{\times}{\overset{CH_3}{\bigcirc}}-\underset{\underset{C_3H_7}{|}}{CH}-\underset{\times}{\overset{CH_3}{\bigcirc}}-O\overset{O}{\underset{\parallel}{C}}-\right]_2}SC_2H_4COOC_{18}H_{37}$$

Bis(2-octadecyloxycarbonylethylenethiolcarbonate) of bis
(4,4′-butylidene-bis(2-t-butyl-5-methylphenol))carbonate.
4.1% thiolcarbonate sulfur.

TABLE 1-continued
THIOLCARBONATE ESTERS

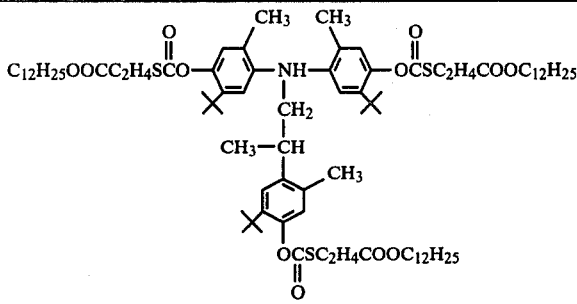

No. 15

Tris(2-dodecyloxycarbonylethylenethiolcarbonate) ester of
1,1,3-tris-(2-methyl-4-hydroxy-5-t-butylphenyl)butane.
6.7% thiolcarbonate sulfur.

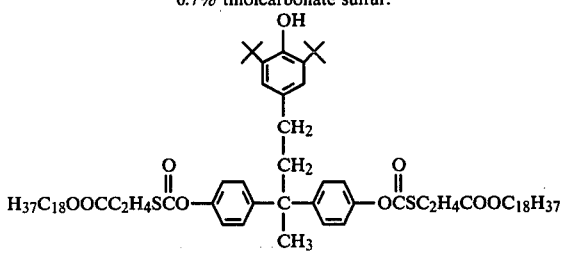

No. 16

1-(3',5',-di-t-butyl-4'-hydroxyphenyl)-3,3-bis(p-2-octadecyloxy-
carbonylethylenethiolcarbonatophenyl)butane. 5.4% thiolcarbonate
sulfur.

The thiolcarbonate esters of this invention can be prepared by the reaction of a carbonylating agent such as phosgene, a chloroformate ester a dialkyl carbonate or a diaryl carbonate with a carboxy alkylenethiol compound and optionally a polyhydroxy compound such as a polyhydric alcohol or phenol in one or several reaction stages. Acid acceptors such as ammonia, pyridine, organic amines, and inorganic alkalies can be used with phosgene and chloroformate esters and acidic or alkaline transesterification catalysts can facilitate the reaction of alkyl and aryl carbonate esters. The molecular weight of the thiolcarbonate ester is regulated by the proportions of carboxyalkylenethiol compound to carbonylating agent and to polyhydric phenol or alcohol when present, as well as the functionality of the carboxyalkylenethiol compound. Thus two moles of a one-functional carboxyalkylenethiol compound react with one mole of carbonylating agent to give a thiolcarbonate of this invention in which p is zero and Q is $$\overset{O}{\underset{\|}{RO CR'S-}},$$

and unreacted carboxyalkylenethiol compound can be separated from the thiolcarbonate ester produced. Two-functional and more highly functional carboxyalkylenethiol compounds react with carbonylating agent while enabling molecular weight to be controlled by suitably proportioning the reactants and by having one-functional carboxyalkylenethiol compound participate in the reaction in the same or a subsequent stage to give rise to thiolcarbonates of this invention in which p is a positive integer and k is one. When the reactants include a polyhydroxy compound, thiolcarbonate esters of the invention in which Q can be $(OX)_m$—AO— and thiolcarbonate esters of the invention in which p is a positive number and k is zero can be obtained. Such preparations as well as the use of various carbonylating agents can be illustrated by reaction equations, in which Ph represents a phenyl group, Et an ethyl group and R, R', A, X, n, and p are as previously defined.

1. Formation of thiolcarbonate ester from carbonylating agent and one-functional carboxyalkylenethiol compound:

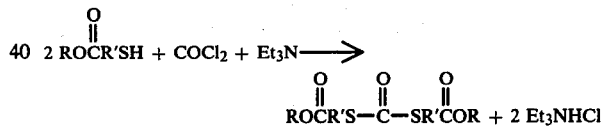

2. 2 stage reactions of diphenyl carbonate carbonylating agent with first a multifunctional and then a one-functional carboxyalkylenethiol compound:

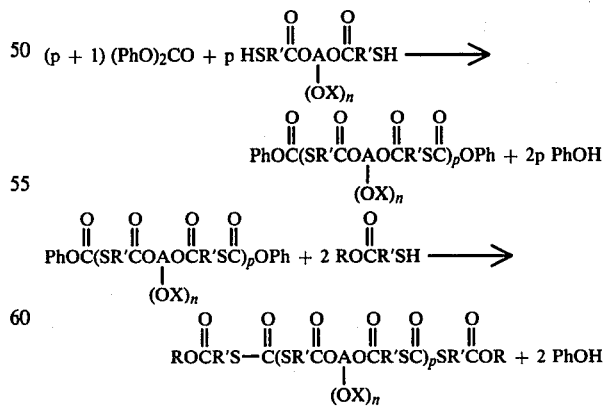

3. 2 stage reaction of chloroformate carbonylating agent with first a one-functional carboxyalkylenethiol compound and then a polyhydroxy compound or a polyhydroxy compound carbonate ester oligomer

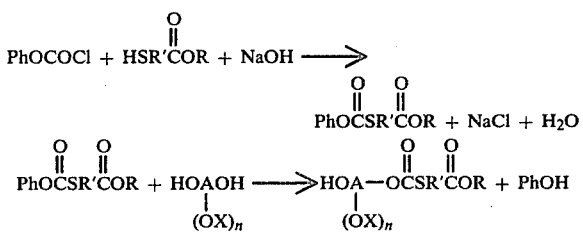

also

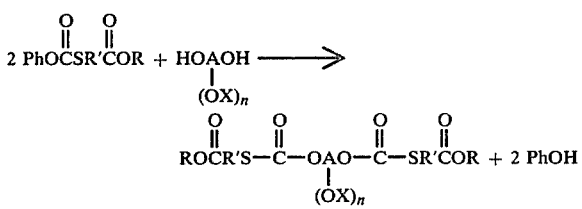

and

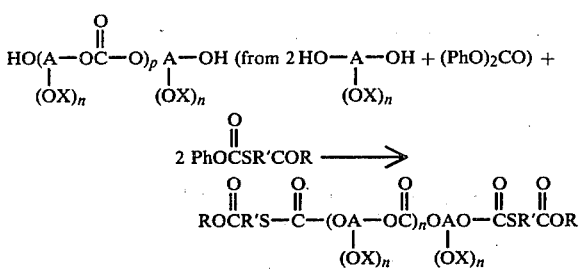

Multifunctional carbonate thiolcarbonate ester of the invention can also be prepared in a single reaction step leading to a random arrangement of carbonic acid ester and thiolcarbonate ester groups in the structure of the coester. Thus the polyhydroxy compound (or mixture of more than one polyhydroxy compound) can be heated with a mixture of diphenyl carbonate and carboxyalkylenethiol-compound with removal of the side-product phenol. Alternatively, the polyhydric phenol or alcohol (or mixture of polyhydroxy compounds) can be reacted, suitably dissolved in an inert solvent such as toluene, methylene chloride or trichloroethylene, with a mixture of carboxyalkylenethiol compound and carbonyl chloride ($COCl_2$) with elimination of by-product hydrogen chloride by reaction with an acid acceptor which can be an organic amine dissolved in the reaction solution, a suspension of an inorganic alkali, or an aqueous solution of an inorganic alkali.

Both the phenyl ester reaction and the acid chloride reaction can be facilitated by the use of catalysts. The phenyl ester reaction is suitably catalyzed by substances of sufficient alkalinity to convert phenol at least in part to the phenoxide ion, such as alkali and alkaline earth metals and their oxides, hydroxides, sulfides, cyanides, phenolates, hydrides, alcoholates, and carboxylates as well as aliphatic and cycloaliphatic amines, preferably tertiary amines to avoid the possible complication of amide formation. Suitable catalysts for the acid chloride reaction include tertiary amines, tertiary phosphines, and the hydrogen halide and alkyl halide addition salts thereof. Catalyst concentrations usefully range from 0.01% to about 5% by weight of reaction mixture. Preferred catalysts for the acid chloride reaction have the ability to partition between water and an immiscible hydrocarbon phase with a partition coefficient between 0.01 and 100.

Both the phenyl ester reaction method of preparing the thiolcarbonate ester of this invention and the acid chloride method can be carried out over a convenient range of reaction temperatures. The phenyl ester reaction is conveniently carried out at elevated temperatures of the order of 80° to 210° C. with removal of the side product phenol by distillation, suitably under diminished pressure. It is frequently helpful to begin the reaction by an atmospheric pressure cook, suitably with nitrogen or other inert gas protection over the reaction mass to preserve its light color, and apply vacuum gradually after a quantity of side product has accumulated for removal.

The acid chloride reaction is conveniently carried out at ambient temperatures or as cold as −15° C. Elevated temperatures in the 40° to 90° C. range can also be used.

The following Examples illustrate, without limiting, the preparation of thiolcarbonate esters according to this invention.

SYNTHETIC EXAMPLE—1

Synthesis of thiolcarbonate ester No. 4, decamethylenebis(2-octadecyloxy carbonylethylenethiolcarbonylthiopropionate) 1,10-Decanediol bis(3-mercaptopropionate) 14.0 g (0.04 mole), diphenylcarbonate 17.1 g (0.08 mole), stearyl-3-mercaptopropionate 28.6 g (0.08 mole) and potassium carbonate 0.06 g were charged, heated and stirred at 150° C. for 3 hours. The phenol produced by the reaction was distilled under the reduced pressure, and the thiolcarbonate ester, a white solid of melting point 57°–60° C. was obtained from the residue after cooling.

SYNTHETIC EXAMPLE—2

Synthesis of thiolcarbonat ester No. 13, 4,4′-butylidenebis (2-t-butyl-5-methylphenyl 2-octadecyloxycarbonylethylenethiolcarbonate): 4,4′-Butylidene bis(3-methyl-6-t-butylphenol) 19.1 g (0.05 mole), diphenylcarbonate 21.4 g (0.1 mole), stearyl-3-mercaptopropionate 35.8 g (0.1 mole) and potassium carbonate 0.08 g were charged heated and stirred at 160° C. for 3 hours. The phenol produced was distilled under reduced pressure, and the residue cooled to obtain a white solid of melting point 75°–80° C.

Synthetic resins that can be stabilized with 0.01 to 5% by weight of a thiolcarbonate ester according to this invention include polymers of alpha-olefin having 2 to 6 carbon atoms such as polyethylene, polypropylene, polybutene, poly-3-methylbutene, or copolymers thereof such as ethylenevinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, polyamide, polycarbonate, polyacetal, polyurethane, cellulosic resin, or phenolic resin, urea resin, melamine resin, epoxy resin, unsaturated polyester, silicon resin, halogen-containing resins such as vinyl chloride polymers, vinylidene chloride polymers, polyvinylidene fluoride and copolymers thereof, and further rubbers such as isoprene rubber, chloroprene rubber, and blends of the above resins.

Stabilizer compositions comprising a thiolcarbonate ester according to this invention together with a known polymer stabilizer can be formulated and marketed in liquid, solid, and paste forms. An inert solvent can be used to facilitate handling. The thiolcarbonate ester and known polymer stabilizers can also be solubilized in one another by heating such as at 70°–160° C. for up to 4 hours, and then allowing the resulting melt to cool and harden sufficiently to be flaked and ground.

Known polymer stabilizers can be used in synthetic resin compositions together with the thiolcarbonate ester stabilizers of this invention and can be admixed with the latter. Such stabilizers include thiodipropionic acid esters, phenols, polyvalent metal salts of carboxylic acids, organic phosphites, 1,2-epoxides, polyhydric alcohols, polyhydric alcohol 3-alkylthiopropionic acid esters, ultraviolet absorbers and heavy metal deactivators.

Representative thiodipropionic acid esters include di-n-dodecyl thiodipropionate dihexadecyl thiodipropionate, distearyl thiodipropionate n-octyleicosanyl thiodipropionate and n-octadecyl cyclohexene-1,4-dimethanol thiodipropionate polyester. A comprehensive disclosure of useful thiodipropionate esters by M. Minagawa et al in U.S. Pat. No. 3,869,423 column 17 line 55 to column 19 line 54 is here incorporated by reference. When thiodipropionate esters are used the concentration based on 100 parts of polymer can range from 0.05 to about 0.75 parts by weight.

Representative phenols include 2,6-di-t-butyl-p-cresol (BHT), 2,2-diphenylolpropane, 1,1,3-tris(2-methyl-4-hydroxy-5-t-butylphenyl)butane, and 1,3,5-tris(3,5-tris(3,5-di-t-butyl-4-hydroxybenzyl)isocyanurate. A comprehensive disclosure of useful phenol stabilizers by M. Minagawa et al in U.S. Pat. No. 3,907,517 column 17 line 64 to column 23 line 61 is here incorporated by reference. When phenols are used, the concentration per 100 parts of polymer being stabilized can range from 0.02 to about 1 part by weight.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 to column 20 line 35 is here incorporated by reference. When metal salts are used the concentration based on 100 parts by weight of polymer can range from 0.1 to about 3 parts by weight.

Representative organic phosphites include triisodecylphosphite, tris (nonylphenyl phosphite), and 4,4'-isopropylidene diphenol alkyl ($C_{12}$–$C_{15}$) phosphite. A comprehensive disclosure of usseful organic phosphites by M. Minagawa in U.S. Pat. No. 3,849,370 column 13 line 63 to column 16 line 48 is here incorporated by reference. Typical use concentrations of organic phosphites are in the range from 0.02 part to about 2 parts by weight per 100 parts of polymer being stabilized.

Representative 1,2-epoxides that can be used in stabilizer compositions according to this invention include epoxyoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference. Typical use concentrations of 1,2-epoxides range from 0.3 to about 6 parts by weight per 100 parts of synthetic resin composition.

Aliphatic polyhydroxy compounds can be included with stabilizer compositions of this invention in amounts corresponding to 0.1 to about 1 part per 100 parts of polymer being stabilized. Typical aliphatic polyhydroxy compounds are glycerol, polyglycerol, mono-, di-, and tri-pentaerythritol, mannitol, sorbitol, and partial esters of these with saturated and unsaturated fatty acids having 6 to 22 carbon atoms.

3-Alkylthiopropionates of polyhydric alcohols can be included in stabilizer compositions of this invention in amounts corresponding to 0.02 to about 1 part per 100 parts of synthetic resin being stabilized. The propionate esters have 4 to about 34 carbon atoms in the alkylthiopropionate group, 2 to about 15 carbon atoms in the polyhydric alcohol group and 2to about 8 ester groups in the molecule. Representative propionate esters are 2,2-dimethylpropanediol bis (3-n-dodecylthio-2-methylpropionate), pentaerythriol tetrakis(3-n-octylthiopropionate) and tris (3-n-octadecylthiopropionyloxyethyl)isocyanurate. For a further listing of useful 3-alkylthiopropionates the disclosure of A. Onishi U.S. Pat. No. 3,629,194 can be consulted.

Ultraviolet absorbers can be included in stabilizer compositions of this invention in amounts corresponding to 0.05 to about 1 part per 100 parts of synthetic resin being protected. Typical ultraviolet absorbers are 2-hydroxybenzophenone such as 2-hydroxy-4-n-octyloxybenzophenone and 2,4-dihydroxybenzophenone, and 2-(2'-hydroxyphenyl)benzotriazoles such as 2-(2'-hydroxy-5'-methylphenylbenzotriazole and 2-(2'-hydroxy-5'-t-butylphenyl) 5,6-dichlorobenzotriazole. For a further listing of many useful ultraviolet absorbers the disclosure of U.S. Pat. No. 3,395,112 of July 30, 1968, particularly column 14 line 40 to column 19 line 33, can be consulted. Stabilizer compositions according to this invention that protect synthetic resin compositions used in contact with materials containing heavy metals and their compounds, as in insulating materials for copper based electrical conductors or in compositions pigmented with heavy metal containing pigments such as rouge, talc, and iron-bearing asbestos, can contain heavy metal deactivators that counteract the prodegradant effect of the heavy metal on synthetic resin compositions that would be satisfactorily stabilized in the absence of heavy metal. Heavy metal deactivators that can be used in stabilizer compositions according to this invention include melamine, dicyandiamide, oxanilide, N,N'-disalicyloylhyrazine, 3-salicycloylamido-1,2,4-triazole, as well as the heavy metal deactivators disclosed by M. Minagawa in U.S. Pat. Nos. 3,549,572 (column 5 line 19 to column 10 line 23), 3,629,181 (column 5 line 15 to column 9 line 54), 3,673,152 (column 4 line 47 to column 8 line 62), and 3,849,370 (column 5 line 5 to column 13 line 45). These disclosures are here incorporated by reference. Illustrative of stabilizer compositions comprising thiolcarbonate esters according to this invention together with known polymer stabilizers are the following:

| STABILIZER COMPOSITION | INGREDIENTS | PARTS BY WEIGHT |
|---|---|---|
| I | S-octadecyloxycarbonylethylenethiol-S'-carboxyethylenethiolcarbonate | 10 |
| | Zinc stearate | 20 |

-continued

| STABILIZER COMPOSITION | INGREDIENTS | PARTS BY WEIGHT |
|---|---|---|
| | Magnesium benzoate | 15 |
| | Mannitol | 25 |
| II | Bis-isodecyloxycarbonylethylenethiolcarbonate of bis(3-methyl-4-hydroxy-5-t-butylbenzyl) sulfide | 12 |
| | Barium nonylphenolate | 30 |
| | Zinc 2-ethylhexoate | 18 |
| | Diphenyl isodecyl phosphite | 40 |
| III | 1,4-butanebis(2-ethylhexyloxycarbonylmethylenethiolcarbonate) | 25 |
| | 2-ethylhexyl epoxystearate | 45 |
| | tris(nonylphenyl) phosphite | 30 |
| IV | 4-(2'-methyl-4'-hydroxy-5'-t-butylalphapropyl benzyl)-2-t-butyl-5-methylphenyl 5-tetradecyloxycarbonylethylene thiolcarbonate | 25 |
| | Distearyl thiodipropionate | 45 |
| | Trihexadecyl phosphite | 10 |

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylene-vinyl acetate copolymers and others.

The Examples that follow illustrate the invention without limiting its scope. The Examples illustrate the use of thiolcarbonate stabilizers of this invention and stabilizer compositions comprising thiolcarbonate esters of this invention in the stabilization of olefin polymers, a vinyl chloride polymer, an ABS polymer, and a polyamide.

EXAMPLES 1-1 TO 1-8

Substantially unstabilized polypropylene (Profax 6501, containing a trace of BHT antioxidant to protect the polymer during shipment and storage only) 100 parts, 1,1,3-tris(2-methyl-4-hydroxy-5-t-butylphenyl)-butane 0.1 part, and additive test candidate 0.2 part by weight were hand-mixed in a hemispherical bowl and fluxed on a two roll mill at 170° C. for 5 minutes. Samples of each milled sheet were compression molded at 180°±3° C. for 5 minutes to give smooth sheets 1.0 in thickness. Strips 10 by 2 cm were cut from each molded sheet and exposed lying flat on aluminum foil in an air circulating oven at 160° C. until found to be embrittled and/or visibly degraded. The additive test candidate present in each sample and the observed time to embrittlement and/or visible degradation in the oven at 160° C. are shown in TABLE-2.

TABLE 2

| NO. | ADDITIVE TEST CANDIDATE | HEAT STABILITY hrs. |
|---|---|---|
| Control | | |
| 1-1 | dilaurylthiodipropionate | 286 |
| 1-2 | distearylthiodipropionate | 320 |
| EXAMPLE | | |
| 1-1 | Thiolcarbonate ester No. 1 | 824 |
| 1-2 | Thiolcarbonate ester No. 2 | 1,020 |
| 1-3 | Thiolcarbonate ester No. 5 | 883 |
| 1-4 | Thiolcarbonate ester No. 7 | 917 |
| 1-5 | Thiolcarbonate ester No. 9 | 955 |
| 1-6 | Thiolcarbonate ester No. 11 | 806 |
| 1-7 | Thiolcarbonate ester No. 13 | 942 |

TABLE 2-continued

| NO. | ADDITIVE TEST CANDIDATE | HEAT STABILITY hrs. |
|---|---|---|
| 1-8 | Thiolcarbonate ester No. 15 | 1,012 |

The results of these heat stability tests demonstrate the dramatic effect of thiolcarbonate esters of this invention in providing together with a trihydric phenol well over twice the heat stability, and in two instances even more than three times the heat stability, of polypropylene samples containing equal amounts of the same trihydric phenol together with a conventional thiodipropionate ester stabilizer.

EXAMPLES 2-1 TO 2-8

Polyethylene resin (Hi-Zex 5100E, Mitsui Petrochemical Industries, Ltd. Japan) 100 parts by weight and a test compound 0.15 part by weight were milled on a two roll mill for 5 minutes at 150° C. and then molded into a sheet of 1.2 mm thickness by compression molding at 150° C. and 180 kg/cm$^2$ for 5 minutes. The sheet was cut into sample pieces of 10×20 mm and tested for heat stability in the Geer oven at 150° C. in air on aluminum foil. The time to the beginning of degradation was taken as the time when more than five sample pieces in ten of each formulation were discolored and brittle. The test compounds used and the results obtained are shown in TABLE 3.

TABLE 3

| No. | TEST COMPOUND | TIME TO DETERIORATION hrs. |
|---|---|---|
| Control | | |
| 2-1 | None | 190 |
| 2-2 | distearylthiodipropionate | 305 |
| 2-3 | BHT | 284 |
| EXAMPLE | | |
| 2-1 | Thiolcarbonate ester No. 3 | 430 |
| 2-2 | Thiolcarbonate ester No. 4 | 419 |
| 2-3 | Thiolcarbonate ester No. 6 | 453 |
| 2-4 | Thiolcarbonate ester No. 8 | 400 |
| 2-5 | Thiolcarbonate ester No. 9 | 437 |
| 2-6 | Thiolcarbonate ester No. 14 | 423 |
| 2-7 | Thiolcarbonate ester No. 15 | 456 |
| 2-8 | Thiolcarbonate ester No. 16 | 424 |

The results of these heat stability tests demonstrate that thiocarbonate esters of this invention are highly effective stabilizers for polyethylene without requiring the presence of other stabilizing additives, more so than a conventional phenolic antioxidant or a conventional thiodipropionate ester stabilizer.

EXAMPLES 3-1 to 3-8

In order to examine the effects of the stabilizer according to this invention on polybutene resin, a sheet of 1 mm in thickness was prepared by kneading the following formulation on a two roll mill and then compression molding at 160° C. and 200 kg/cm$^2$ for 5 minutes. The sheet obtained was cut to the size of 40×150 mm and suspended in an individual glass cyclinder.

Each cylinder was set in an air circulating oven at 160° C., flushed with pure oxygen, the pressure adjusted to one atmosphere, and the cyclinder fitted with a closed end manometer.

| (Formulation) | |
|---|---|
| Un-stabilized poly-1-butene resin | 100 parts by weight |
| Calcium stearate | 1.0 |
| Stearyl beta(3,5-di-t-butyl-4-hydroxyphenyl)propionate | 0.2 |
| Sample compound | 0.2 |

The results are shown in TABLE 4. The time to beginning of deterioration was read by recording the time when the pressure in the cylinder diminished rapidly.

TABLE 4

| No. | SAMPLE COMPOUND | TIME TO DETERIORATION hrs. |
|---|---|---|
| Control | | |
| 3-1 | dilaurylthiodipropionate | 340 |
| EXAMPLE | | |
| 3-1 | Thiolcarbonate ester No. 1 | 705 |
| 3-2 | Thiolcarbonate ester No. 3 | 750 |
| 3-3 | Thiolcarbonate ester No. 6 | 690 |
| 3-4 | Thiolcarbonate ester No. 7 | 720 |
| 3-5 | Thiolcarbonate ester No. 10 | 735 |
| 3-6 | Thiolcarbonate ester No. 12 | 715 |
| 3-7 | Thiolcarbonate ester No. 13 | 720 |
| 3-8 | Thiolcarbonate ester No. 16 | 735 |

The results of these heat stability tests demonstrate that thiocarbonate esters of this invention are at least twice as effective as a conventional thiodipropionate ester in the stabilization of poly-1-butene together with a calcium salt and a phenolic antioxidant. Since the tests are carried out in a closed system, the effect of volatility differences is minimized and a true comparison of stabilizing effectiveness is obtained.

EXAMPLES 4-1 TO 4-8

ABS resin (Blendex 111) 100 parts by weight, zinc stearate 0.5 part by weight, titanium oxide 5.0 parts by weight and sample compound 0.5 part by weight were mixed by grinding at room temperature for 10 minutes.

The compound was prepared by extruding the ground mixture using a 30 mm extruder at 30 rpm and 240° C. A sheet of 0.5 mm thickness was prepared by compression molding each extruded compound at 200 kg/cm² and 180° C. for 5 minutes. Each molded sheet was cut to the size of 40×150 mm, and suspended in an individual glass cylinder.

Each cylinder was set in an air circulating oven at 140° C., flushed with pure oxygen, the pressure adjusted to one atmosphere, and the cylinder fitted with a closed end manometer.

The time to beginning of deterioration was read by recording the time when the pressure in the cylinder diminished rapidly. The sample compound used in each example and the results observed are shown in TABLE 5.

TABLE - 5

| No. | SAMPLE COMPOUND | TIME TO DETERIORATION Min. |
|---|---|---|
| Control | | |
| 4-1 | None | 150 |
| 4-2 | dilaurylthiodipropionate | 220 |
| EXAMPLE | | |
| 4-1 | Thiolcarbonate ester No. 2 | 580 |
| 4-2 | Thiolcarbonate ester No. 4 | 510 |
| 4-3 | Thiolcarbonate ester No. 5 | 520 |
| 4-4 | Thiolcarbonate ester No. 8 | 490 |
| 4-5 | Thiolcarbonate ester No. 10 | 500 |
| 4-6 | Thiolcarbonate ester No. 11 | 560 |
| 4-7 | Thiolcarbonate ester No. 12 | 570 |
| 4-8 | Thiolcarbonate ester No. 14 | 530 |

The results of these heat stability tests demonstrate that thiolcarbonate esters of this invention are at least twice as effective as a conventional thiodipropionate ester in the stabilization of ABS polymer together with a zinc salt. Since the tests are carried out in a closed system, the effect of volatility differences is minimized and a true comparison of stabilizing effectiveness is obtained.

EXAMPLES 5-1 to 5-8

A clear sheet was prepared by kneading polyvinylchloride resin (Geon 103 EP) 100 parts dioctylphthalate 42 parts, epoxidized soybean oil 3 parts, zinc stearate 0.3 part, barium stearate 0.5 part, stearic acid 0.3 part, and a sample compound 0.2 part on a two roll mill at 175° C. for 5 minutes and then compression molding at 175° C. Then, a heat stability test was carried out in a Geer oven at 190° C. in an air atmosphere. The time to degradation was determined by the discoloration observed. The sample compound used and the results obtained are shown in TABLE 6.

TABLE 6

| NO | SAMPLE COMPOUNDS | TIME TO DEGRADATION YELLOWED Min. | BLACKENED Min. |
|---|---|---|---|
| Control | | | |
| 5-1 | None | 30 | 40 |
| 5-2 | dilaurylthiodipropionate | 40 | 50 |
| 5-3 | dioctyltinbis(iso-octylthiodiglycolate | 45 | 60 |
| EXAMPLE | | | |
| 5-1 | Thiolcarbonate ester No. 1 | 60 | 75 |
| 5-2 | Thiolcarbonate ester No. 3 | 60 | 80 |
| 5-3 | Thiolcarbonate ester No. 4 | 60 | 75 |
| 5-4 | Thiolcarbonate ester No. 6 | 65 | 80 |
| 5-5 | Thiolcarbonate ester No. 8 | 65 | 85 |
| 5-6 | Thiolcarbonate ester No. 10 | 60 | 80 |
| 5-7 | Thiolcarbonate ester No. 13 | 70 | 90 |
| 5-8 | Thiolcarbonate ester No. 15 | 65 | 85 |

The results of these heat stability tests demonstrate that thiocarbonate esters are highly effective in enhancing the effectiveness of known stabilizers for PVC.

In the time required to degrade control PVC formulations to a blackened condition, PVC with a thiolcarbonate ester according to this invention had reached no more than a yellow stage, that is a condition in which the resin remained processable.

EXAMPLES 6-1 TO 6-5

100 parts of nylon 66 delustered by adding 0.05% of titanium dioxide was dissolved in 90 parts of 90% formic acid, and 1.0 part of sample compound was added and mixed completely. The solution was flowed uniformly on a glass plate, and dried in a heated air oven at 105° C. for 10 minutes to prepare a film. The color of the film, after being heated in an air oven at 225° C. for 30 minutes, was measured and shown in TABLE 7 along with the compounds present in each formulation.

TABLE 7

| No. | SAMPLE COMPOUND | COLOR OF SHEET |
| --- | --- | --- |
| Control | | |
| 6-1 | None | Dark brown |
| EXAMPLE | | |
| 6-1 | Thiolcarbonate ester No. 2 | Light yellow |
| 6-2 | Thiolcarbonate ester No. 5 | Light yellow |
| 6-3 | Thiolcarbonate ester No. 7 | Light yellow |
| 6-4 | Thiolcarbonate ester No. 11 | Light yellow |
| 6-5 | Thiolcarbonate ester No. 14 | Light yellow |

The results of these tests show the powerful effectiveness of thiolcarbonate esters of this invention in preventing the darkening of polyamide plastic upon heating at a high temperature even in the absence of any other stabilizing additives.

EXAMPLES 7-1 TO 7-8

In order to examine the effects of the thiolcarbonate esters according to this invention in ethylene-vinylacetate copolymer, samples were prepared according to the following formulation and tested for heat stability in a Gear oven at 175° C. and initial color was measured for yellowness using the Hunter color difference meter, greater numbers indicating more severe discoloration.

The results are shown in Table 8. The heat stability is expressed in minutes of heating in the oven until a red or brown discoloration was observed.

| (Formulation) | |
| --- | --- |
| Ethylene-Vinyl copolymer resin | 100 parts |
| Montan wax ester lubricant | 0.3 |
| Sample compound | 0.1 |

Table 8

| No. | SAMPLE COMPOUND | HEAT STABILITY min. | INITIAL COLOR |
| --- | --- | --- | --- |
| Control | | | |
| 7-1 | None | 75 | 33 |
| 7-2 | dilaurylthiodipropionate | 90 | 26 |
| Example | | | |
| 7-1 | Thiolcarbonate ester No. 1 | 120 | 9 |
| 7-2 | Thiolcarbonate ester No. 3 | 150 | 10 |
| 7-3 | Thiolcarbonate ester No. 6 | 135 | 11 |
| 7-4 | Thiolcarbonate ester No. 8 | 135 | 10 |
| 7-5 | Thiolcarbonate ester No. 11 | 150 | 12 |
| 7-6 | Thiolcarbonate ester No. 12 | 120 | 11 |
| 7-7 | Thiolcarbonate ester No. 14 | 135 | 9 |
| 7-8 | Thiolcarbonate ester No. 16 | 135 | 10 |

The results of these tests demonstrate the dramatic effectiveness of thiolcarbonate esters of this invention in preserving the good initial color and improving heat stability of ethylene-vinyl acetate copolymer. In comparison, the conventional thiodipropionate ester stabilizer has only a marginally favorable effect. Moreover, no other stabilizing additive is needed in the formulation to obtain the dramatic stabilizing effectiveness of the thiolcarbonate esters in ethylene-vinyl acetate copolymer.

EXAMPLES 8-1 TO 8-8

The stabilizer combinations according to this invention have an excellent stabilizing effect on crosslinked polyethylene. Unstabilized low density polyethylene (meltindex 2.0) 100 parts by weight, 4,4'-thiobis(3-methyl-6-t-butylphenol) 0.2 part by weight, and a sample compound 0.2 part by weight were mixed by milling on a two roll mill at 110° C. for 10 minutes and then dicumyl peroxide (Percumyl D, Nippon Oil and Fats Co., Ltd.) 2.0 parts by weight was added and further kneaded at the same temperature for two minutes. This sheet prepared on the mill was compression molded at 110° C. and 100 kg/cm$^2$ for 5 minutes, then rapidly heated up to 180° C. while maintaining the pressure at 100 kg/cm$^2$ for 15 minutes. The sheet obtained was cut to the size of 40×150 mm, hung in a Geer oven and tested for heat stability in air at 160° C. The degradation time was judged by looking for the time when more than 50% of pieces were discolored or deformed. The stabilizers ingredients used and the results obtained are shown in TABLE 9.

TABLE 9

| No. | SAMPLE COMPOUND | TIME TO DEGRADATION hrs. |
| --- | --- | --- |
| CONTROL | | |
| 8-1 | dilaurylthiodipropionate | 112 |
| EXAMPLE | | |
| 8-1 | Thiolcarbonate ester No. 2 | 172 |
| 8-2 | Thiolcarbonate ester No. 4 | 160 |
| 8-3 | Thiolcarbonate ester No. 7 | 195 |
| 8-4 | Thiolcarbonate ester No. 9 | 181 |
| 8-5 | Thiolcarbonate ester No. 10 | 185 |
| 8-6 | Thiolcarbonate ester No. 12 | 194 |
| 8-7 | Thiolcarbonate ester No. 13 | 177 |
| 8-8 | Thiolcarbonate ester No. 15 | 189 |

We claim:

1. As a new composition of matter, thiolcarbonate ester having a molecular weight from 400 to 5000, a thiolcarbonate sulfur content from 3 to 20 percent by weight and having the formula:

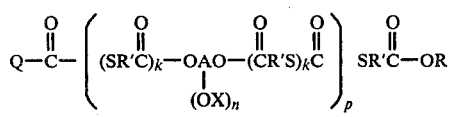

in which R is a hydrogen atom, an aliphatic hydrocarbon group having 1 to 22 carbon atoms, a cycloaliphatic hydrocarbon group having 5 to 22 carbon atoms, or an aromatic hydrocarbon group having 6 to 22 carbon atoms; R' is an alkylene group having 1 to 3 carbon atoms; A is the residue of a polyhydroxy compound having 2 to 40 carbon atoms and 2 to 4 hydroxy groups, provided that the number of hydroxy groups does not exceed the number of carbon atoms; Q is

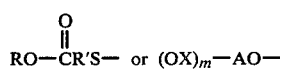

where X individually at each occurrence is a hydrogen atom or

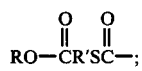

k has the same value at each occurrence and is zero or 1; m is a whole number from 1 to 3; n is a whole number from 0 to 2; and p is a number from 0 to 10.

2. A thiolcarbonate ester according to claim 1 in which R is a hydrocarbon group having 1 to 22 carbon atoms.

3. A thiolcarbonate ester according to claim 1 in which R' is —CH2CH2—.

4. A thiolcarbonate ester according to claim 1 in which A is a residue of an esterified aliphatic or cycloaliphatic dihydric alcohol.

5. A thiolcarbonate ester according to claim 1 in which A is a residue of a polyhydric phenol having the formula:

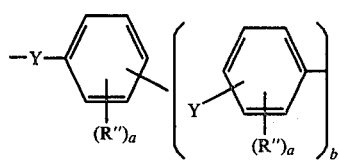

in which independently at each occurrence R" is an alkyl, cycloalkyl, or aralkyl radical having not over 10 carbon atoms, Y is a single bond, oxygen, sulfur,

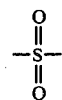

—CH2SCH2—, a bivalent hydrocarbon radical, or

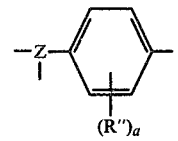

where Z is a hydrocarbon radical, a is a whole number from 0 to 3, and b is zero or one.

6. A thiolcarbonate ester according to claim 1 in which k is zero.

7. A thiolcarbonate ester according to claim 1 in which k is one.

8. A thiolcarbonate ester according to claim 1 in which p is zero.

9. A thiolcarbonate ester according to claim 1 which is S,S'-bis(2-dodecyloxycarbonylethylenethiol) carbonate.

10. A thiolcarbonate ester according to claim 1 which is 1,10-decamethylenebis(2-octadecyloxycarbonylethylenethiolcarbonylthiopropionate).

11. A thiolcarbonate ester according to claim 1 which is 4,4'-butylidenebis(2-t-butyl-5-methylphenyl 2-octadecyloxycarbonylethylenethiolcarbonate).

12. A stabilizer composition capable of increasing the resistance to deterioration on heating of a synthetic resin, comprising a thiolcarbonate ester according to claim 1 and at least one synthetic resin stabilizer selected from the group consisting of thiodipropionate esters, phenols, 1,2-epoxides, organic phosphites, polyhydric alcohols, polyhydric alcohol 3-alkylthiopropionates, ultraviolet absorbers, heavy metal deactivators, and barium, calcium, magnesium, nickel, strontium, tin, and zinc salts of monocarboxylic acids having 6 to 24 carbon atoms.

13. A stabilizer composition according to claim 12 in which the synthetic resin stabilizer is a phenol.

14. A stabilizer composition according to claim 12 in which the synthetic resin stabilizer is a 1,2-epoxide.

15. A stabilizer synthetic resin composition comprising a synthetic resin and 0.01 to 5% by weight of a thiolcarbonate ester according to claim 1.

16. A stabilized synthetic resin composition according to claim 15 in which the synthetic resin is a polymer of an alpha olefin having 2 to 6 carbon atoms.

17. A stabilized synthetic resin composition according to claim 15 in which the synthetic resin is a polymer of vinyl chloride.

18. A stabilized synthetic resin composition according to claim 15 in which the resin is an acrylonitrile-butadienestyrene polymer.

* * * * *